United States Patent

Nakayama

[11] Patent Number: 6,052,474
[45] Date of Patent: *Apr. 18, 2000

[54] METHOD AND APPARATUS FOR COLLATING IMAGES

[75] Inventor: Akihito Nakayama, Tokyo, Japan

[73] Assignee: Sony Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/702,017

[22] Filed: Aug. 23, 1996

[30] Foreign Application Priority Data

Aug. 30, 1995 [JP] Japan .................. P07-245535

[51] Int. Cl.[7] ................ G06K 9/00; G06T 1/00
[52] U.S. Cl. .............. 382/124; 382/278; 382/195
[58] Field of Search ............... 382/112, 124, 382/125, 126, 127, 115, 118, 149, 150, 151, 217, 218, 219, 220, 294, 295, 194, 202, 278, 195; 340/825.34; 356/71

[56] References Cited

U.S. PATENT DOCUMENTS

| | | | |
|---|---|---|---|
| 4,396,903 | 8/1983 | Habicht et al. | 382/9 |
| 4,581,760 | 4/1986 | Schiller et al. | 382/4 |
| 4,944,021 | 7/1990 | Hoshino et al. | 382/125 |
| 5,054,090 | 10/1991 | Knight et al. | 382/127 |
| 5,067,162 | 11/1991 | Driscoll, Jr. et al. | 382/124 |
| 5,093,867 | 3/1992 | Hori et al. | 362/8 |
| 5,146,102 | 9/1992 | Higuchi et al. | 250/556 |
| 5,226,095 | 7/1993 | Okumura et al. | 382/48 |
| 5,325,442 | 6/1994 | Knapp | 382/124 |
| 5,579,415 | 11/1996 | Takano et al. | 382/282 |
| 5,592,573 | 1/1997 | Eisenbarth et al. | 382/294 |
| 5,623,553 | 4/1997 | Sekiya | 382/127 |
| 5,642,434 | 6/1997 | Nakao et al. | 382/220 |
| 5,717,792 | 2/1998 | Poggio et al. | 382/278 |
| 5,719,954 | 2/1998 | Onda | 382/154 |

*Primary Examiner*—Leo H. Boudreau
*Assistant Examiner*—Brian P. Werner
*Attorney, Agent, or Firm*—Ronald P. Kananen; Rader, Fishman & Grauer

[57] ABSTRACT

The present invention provides a method of collating images and an apparatus for collating images capable of collating an image for collation taken in as digital data with an image for reference stored as digital data comparatively simply and surely. There are provided image information extracting means for extracting plural pieces of one-dimensional information from within an image for collation or within an image for reference, positional information group determining means for collating the one-dimensional information with an image for collation or an image for reference of the object, thereby to obtain positional information groups at locations where a coefficient of coincidence of data reaches a set value or higher with respect to respective one-dimensional information, and deciding means for deciding that the image for collation and the image for reference are identical when a combination of data having a relative positional relationship which coincides with the relative positional relationship of the extracted one-dimensional information or is within prescribed dispersion exists among positional information groups obtained with respect to respective one-dimensional information.

20 Claims, 13 Drawing Sheets

EXTRACTION OF ONE-DIMENSIONAL INFORMATION (ONE-DIMENSIONAL LINE)

BINARY-CODED FINGERPRINT IMAGE

SYSTEM BLOCK DIAGRAM

COLLATION PART BLOCK DIAGRAM

COORDINATES OF IMAGE

COLLATION OF ONE-DIMENSIONAL INFORMATION
(ONE-DIMENSIONAL LINE)

(COLLATION IMAGE BY HARDWARE)

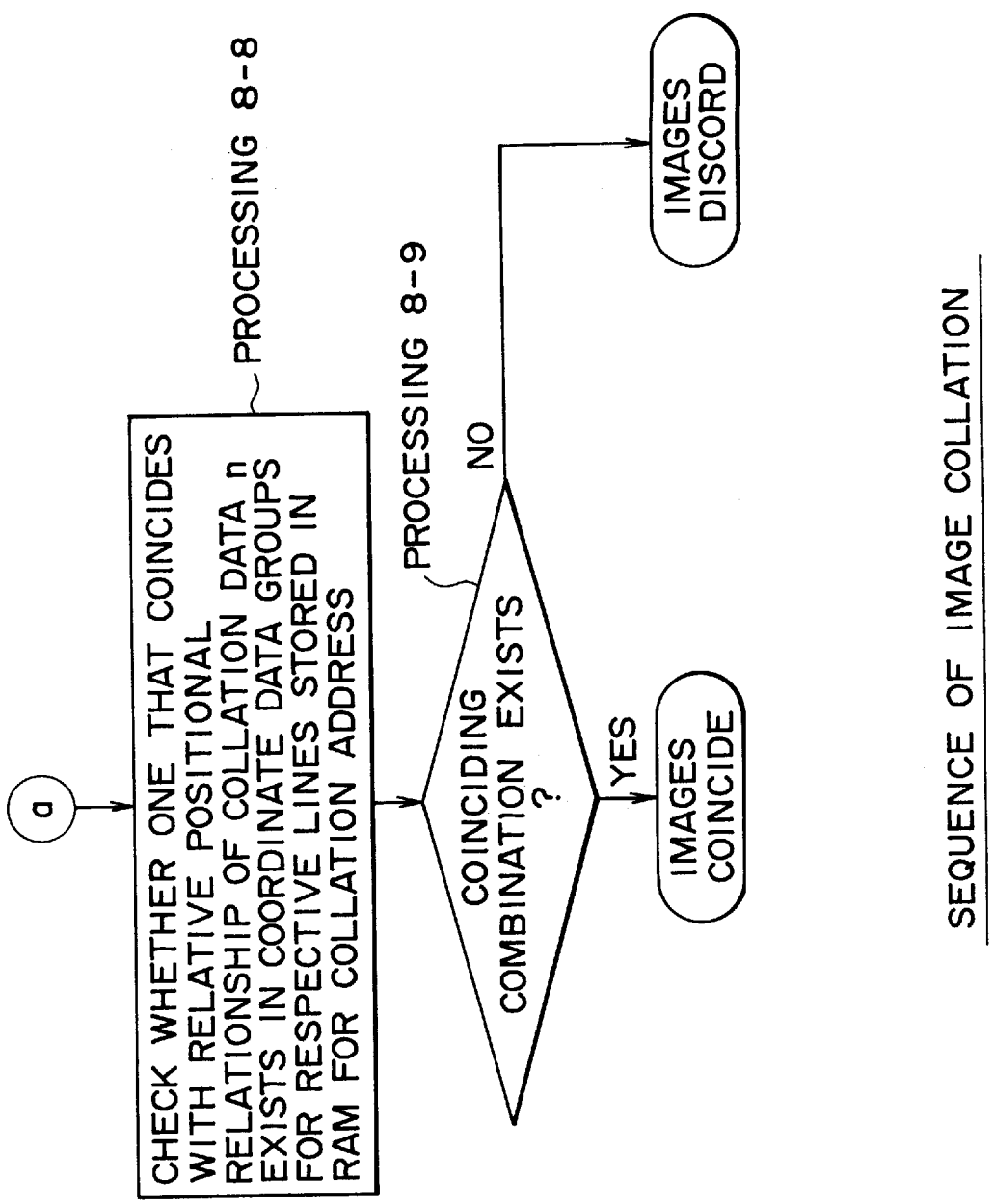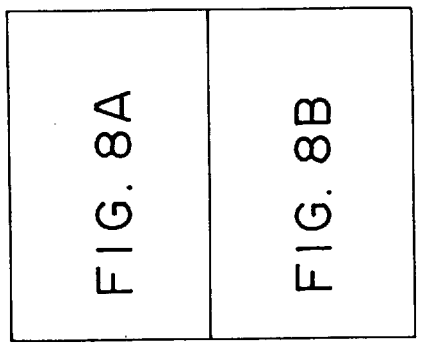

| FIG. 9A |
| FIG. 9B |

RELATIVE POSITIONAL RELATIONSHIP CHECK SEQUENCE

HATCHED PORTION :
OUTSIDE OF DATA EXTRACTION EXTENT SHOWS PERMISSIBLE EXTENT OF DISLOCATION QTY. OF IMAGE
(PERMISSIBLE EXTENT OF DISLOCATION QTY. BETWEEN IMAGE FOR COLLATION AND IMAGE FOR REFERENCE)

EXTRACTION EXTENT OF ONE-DIMENSIONAL INFORMATION (ONE-DIMENSIONAL DATA) AND IMAGE

BLOCK DIAGRAM OF PARALLEL PROCESSING COLLATION PORTION FOR ATTAINING HIGH SPEED

BLOCK DIAGRAM OF COLLATING PORTION OF TWO-DIMENSIONAL SMALL REGION

METHOD AND APPARATUS FOR COLLATING IMAGES

BACKGROUND OF THE INVENTION

The present invention relates to a method of collating images and an apparatus for collating images for collating an image for collation that has been taken in as digital data with an image for reference that has been stored as digital data.

When a fingerprint for instance is collated as a case of comparing an image for collation with an image for reference, the image of a fingerprint for collation taken in from a finger and an image of a fingerprint for reference are collated with each other by extracting features from respective images and paying attention to that portion. As the features, a branch point of a line on an image for instance is extracted. In such conventional collation of images, an image of a fingerprint for collation and an image of a fingerprint for reference are collated with each other based on light and shade of an image, the number of black and white lines of an image, angular information of the line and so forth.

In such a conventional collating system, however, since it is required to extract features of the image for collation and the image for reference, to count the number of black and white lines, to obtain angular information at the black and white portions of the image or to calculate light and shade of an image, complicated calculation processing is required. Further, there are such drawbacks that the processing takes time, the processing apparatus becomes large in scale, and a high speed central processing unit also becomes necessary.

OBJECT AND SUMMARY OF THE INVENTION

Thereupon, the present invention has been made for solving the above-mentioned subjects, and has for its object to provide a method of collating images and an apparatus for collating images that are capable of collating an image for collation that has been taken in as digital data and an image for reference that has been stored as digital data with each other comparatively simply and surely.

According to the present invention, the above-mentioned object is achieved by a method of collating images in which, when an image for collation that has been taken in as digital data and an image for reference that has been stored as digital data are collated with each other, plural pieces of one dimensional information are extracted from within an image for collation or within an image for reference, these pieces of one-dimensional information are made to be collated with the image for collation or the image for reference of the object, and positional information groups at locations where a coefficient of coincidence of the data reaches a set value or higher are obtained with respect to respective one-dimensional information, and it is determined that the image for collation and the image for reference are identical when a combination of data having a relative positional relationship which coincides with the relative positional relationship of the extracted one-dimensional information or is within prescribed dispersion exists among positional information groups obtained with respect to respective one-dimensional information.

According to the present invention, plural pieces of one-dimensional information are extracted from an image for collation or an image for reference, and these pieces of one-dimensional information are collated with the image of the object. Thus, positional information groups at locations (points) when a coefficient of coincidence of data with respect to respective one-dimensional information reaches a setting reference are obtained.

Then, when a combination of data having a relative positional relationship which coincides with the relative positional relationship of the extracted one-dimensional information or is within prescribed dispersion exists among positional information groups, it is decided that the image for collation and the image for reference are identical.

With this, it is possible to surely decide whether an image for collation and an image for reference are identical or not by collating the image for collation that has been taken in as digital data with the image for reference that has been stored as digital data.

According to the present invention, the above-mentioned object is achieved by means of an apparatus for collating images for collating an image for collation that has been taken in as digital data with an image for reference that has been stored in advance as digital data, provided with image information extracting means for extracting plural pieces of one-dimensional information from within an image for collation or within an image for reference, positional information group determining means for collating these pieces of information with an image for collation or an image for reference of the object and obtaining positional information groups at locations where a coefficient of coincidence of data reaches a set value or higher with respect to respective one-dimensional information, and deciding means for deciding that the image for collation and the image for reference are identical when a combination of data having a relative positional relationship which coincides with the relative positional relationship of the extracted one-dimensional information or is within prescribed dispersion exists among positional information groups obtained with respect to respective pieces of one-dimensional information.

According to the present invention, the image information extracting means extracts plural pieces of one-dimensional information from an image for collation or an image for reference. The positional information group determining means has the obtained plural pieces of one-dimensional information collate with the image of the object, thereby to obtain the positional information groups at locations where a coefficient of coincidence of data reaches a set value or higher with respect to respective pieces of one-dimensional information. Further, the deciding means decides that the image for collation and the image for reference are identical when a combination of data having a relative positional relationship which coincides with the relative positional relationship of the extracted one-dimensional information or is within prescribed dispersion exists among positional information groups.

With this, it is possible to surely decide whether an image for collation and an image for reference are identical or not by collating the image for collation that has been taken in as digital data with the image for reference that has been stored as digital data.

BRIEF DESCRIPTION OF THE DRAWINGS

FIG. 8, comprising FIGS. 8A and 8B, is a chart showing a sequence of image collation in an apparatus for collating images;

DESCRIPTION OF THE PREFERRED EMBODIMENTS

Preferred embodiments of the present invention will be described in detail hereinafter with reference to the accompanying drawings.

Besides, since the embodiments described hereunder are preferred exemplifications of the present invention, various technically preferred limitations are provided. The scope of the present invention is, however, not limited to these embodiments unless it is specified in particular to limit the present invention in the description hereinafter.

The embodiment 1 to the embodiment 3 described hereinafter show examples that an apparatus for collating images is applied to the collation of a fingerprint.

Embodiment 1

Figure 1:
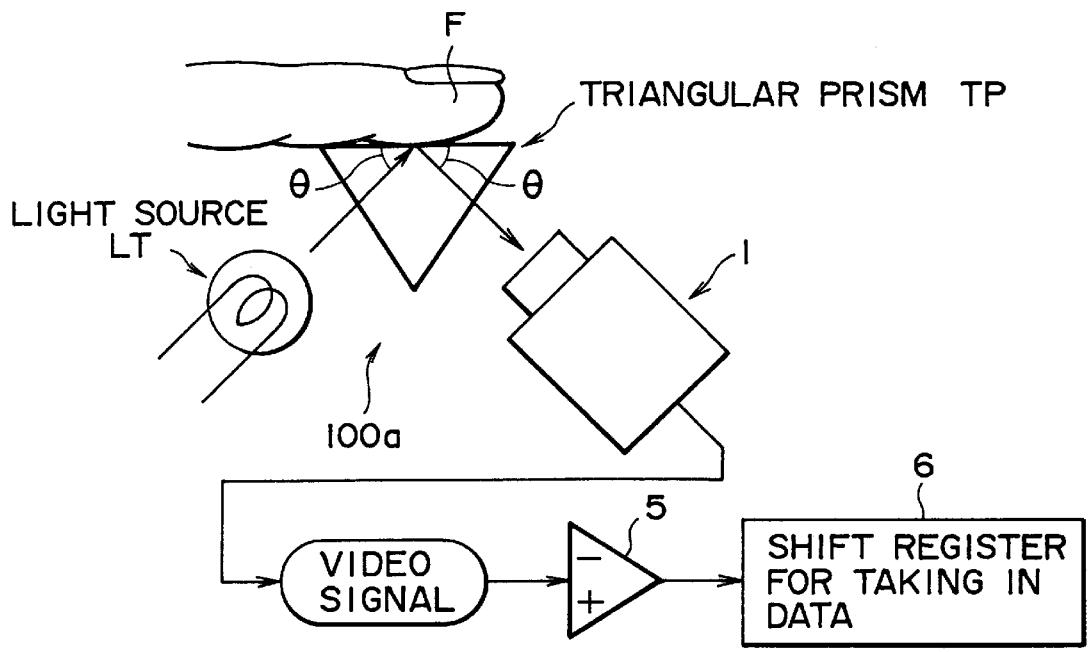
FIG. 1 is a diagram showing an example of a fingerprint image take-in portion of an apparatus for collating images according to the present invention.
Figure 3:
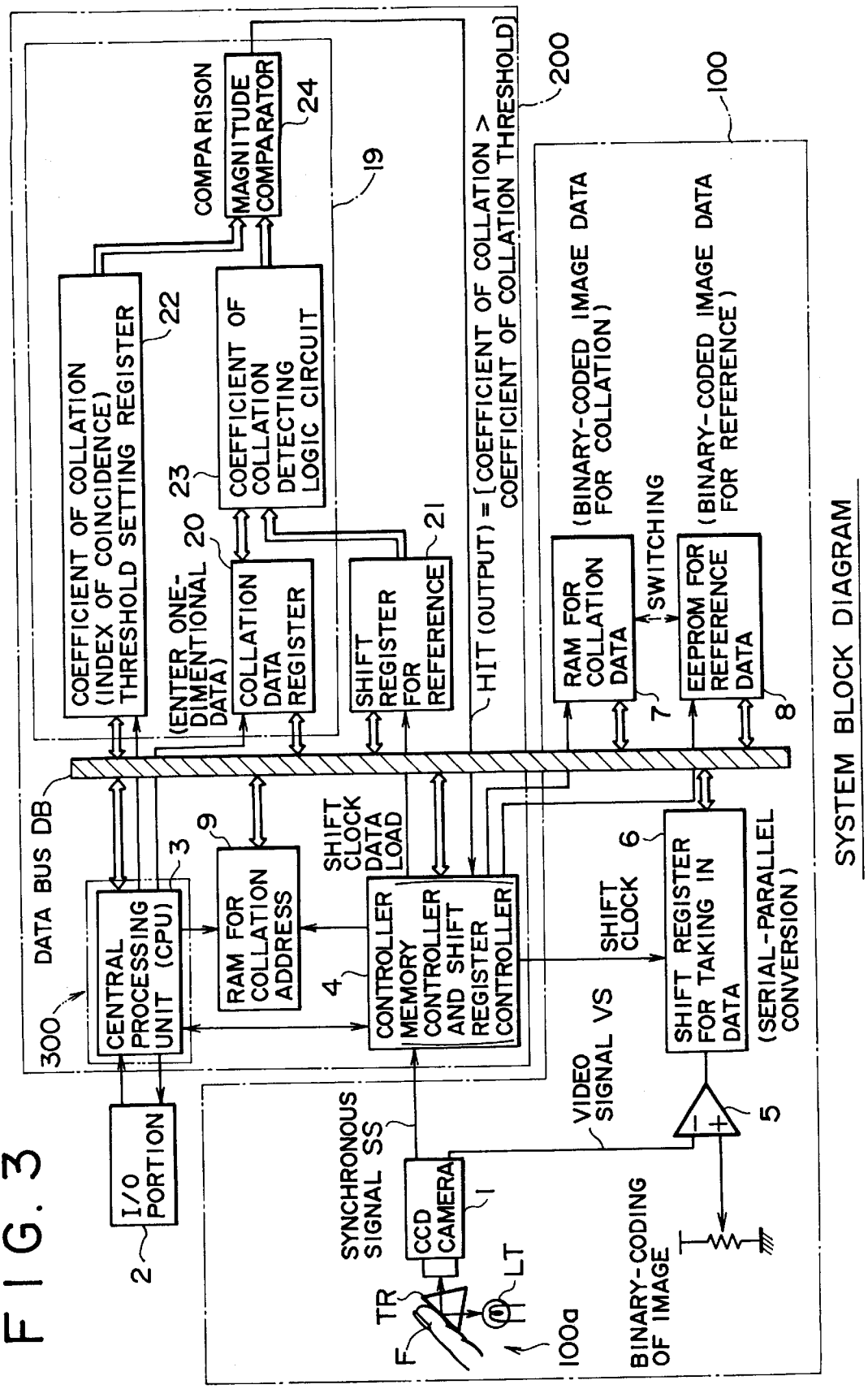
FIG. 3 is a system block diagram showing an embodiment 1 of an apparatus for collating images according to the present invention.

FIG. 1 shows a fingerprint image take-in portion 100a for taking in an image of a fingerprint of a finger F which is an object an image of which is being taken in and supplying the image to an apparatus for collating images shown in FIG. 3.

Figure 2:
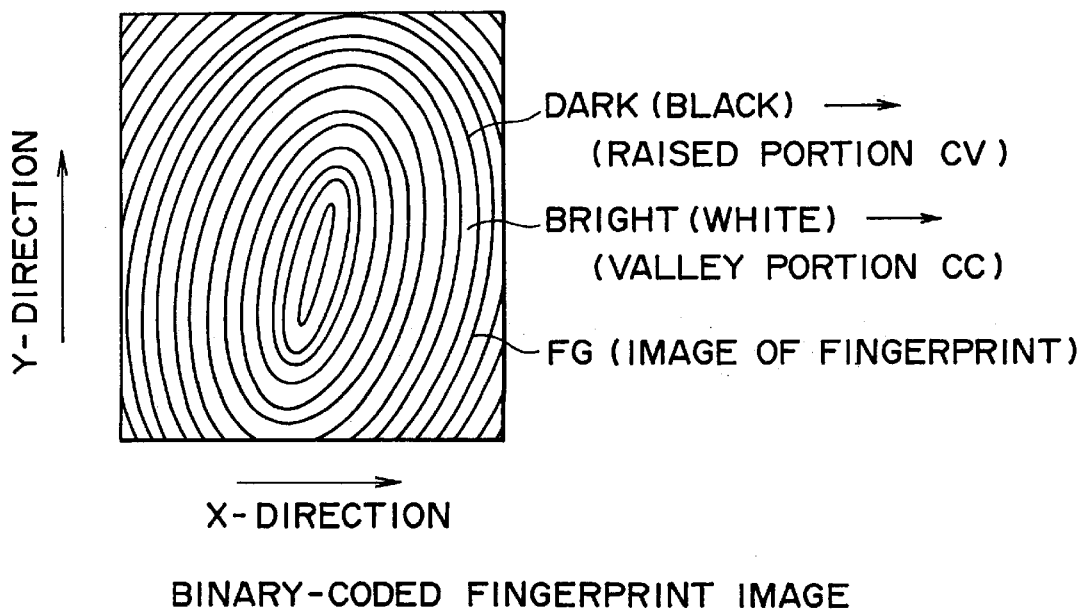
FIG. 2 is a diagram showing an example of a fingerprint image taken in by the fingerprint image taking-in portion shown in FIG. 1.

The fingerprint image take-in portion 100a—shown in FIG. 1 is provided with a triangular prism TP, a light source LT and a charge coupled device (CCD) camera 1. The light from the light source LT is incident upon the triangular prism TP at an angle θ and is totally reflected at an angle θ from a plane of the triangular prism where the finger is placed, thereby to take the fingerprint information of the finger F into the CCD camera 1. In this case, the light of the light source LT is reflected diffusedly from raised parts of the fingerprint, and is reflected totally from valley parts of the fingerprint. When the reflected light at the raised parts and the valley parts of the fingerprint are imaged on the CCD camera 1, a fingerprint image in which raised parts CV are dark and valley parts CC are bright as shown in FIG. 2 is obtainable. FIG. 2 shows an example of an image in which this fingerprint image FG is binary coded. In the example of an image shown in FIG. 2, the dark parts are shown black and the bright parts are shown white. Therefore, the dark parts show the raised parts CV of the fingerprint and the bright parts are the valley parts CC of the fingerprint.

Figure 5:
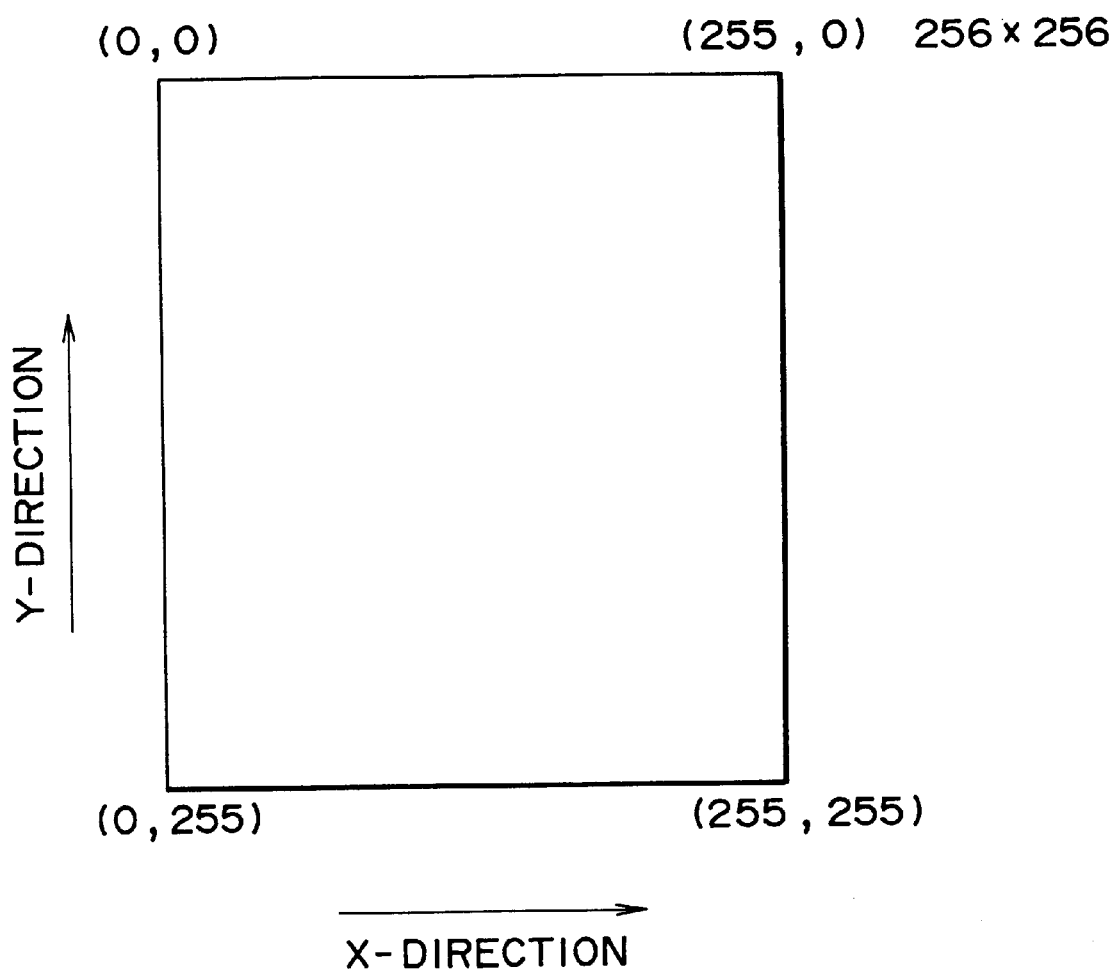
FIG. 5 is a diagram for explaining coordinates of an image of the fingerprint shown in FIG. 2.

When it is assumed that, in the fingerprint image information taken in by the CCD camera 1 shown in FIG. 1, a horizontal direction is an X-direction and a vertical direction is a Y-direction as shown in FIG. 5, sampling on 256 signals is made thereby to perform quantization. With this, coordinates can be formed as shown in FIG. 5 for the fingerprint FG shown in FIG. 2, and optional information of the fingerprint FG can be expressed using two coordinates in the X- and Y-directions. Besides, in the present apparatus for collating images, the number of sampling is set to 256, which, however, is not limited thereto, but it is possible to optimize the number of sampling for each apparatus for collating fingerprints depending on the number of raised lines and the number of black and white in the image.

Next, reference is made to FIG. 3. FIG. 3 is a system block diagram showing a preferred embodiment of an apparatus for collating images according to the present invention.

In FIG. 3, an apparatus for collating images used as an apparatus for collating fingerprints includes an image information extracting means 100, a positional information group determining means 200, a deciding means 300 and so on.

The image information extracting means 100 is composed of a fingerprint image take-in portion 100a, a comparator 5, a shift register 6 for taking in data, a RAM 7 for collation data, and an EEPROM 8 for reference data.

The CCD camera 1 which converts a fingerprint image into a video signal VS by imaging it outputs a synchronous signal SS and a video signal VS. The synchronous signal SS is given to a controller 4 which will be described later. Further, the video signal VS is inputted to a minus input terminal side of the comparator 5. This comparator 5 is a circuit for binary coding the data with the video signal VS from the CCD camera 1 as a reference value, and the data are supplied to a shift register 6 for taking in data as serial data.

The shift register 6 for taking in data converts serial data that have been binary coded by the comparator 5 into parallel data, and the data converted into parallel data are transferred to the RAM 7 for collation data through a data bus DB in the case of a collation image of a fingerprint, and are transferred to the EEPROM 8 for reference data and stored therein in the case of a reference image of a fingerprint.

In a word, the RAM 7 for collation data is a random access memory for storing image data for collating a fingerprint that have been taken in from the finger F and binary coded. The EEPROM 8 for reference data is a read only memory (an electrically erasable programmable read only memory) for storing binary coded image data for reference of a fingerprint in advance.

With this, the binary-coded image data for reference of a fingerprint are transferred to the EEPROM 8 for reference data and stored therein, whereas the binary coded data of an image for collation of a fingerprint are transferred to the RAM 7 for collation and stored therein. With this, when the data for reference (registration) are taken in, binary coded data obtained by binary coding of the video signal VS by means of the comparator 5 and serial-to-parallel conversion by the shift register 6 are stored in the EEPROM 8 for reference data. Further, at time of taking in collation data, the serial-parallel converted data are transferred to the RAM 7 for collation data and stored therein.

Besides, switching of collation to and from reference is made by the central processing unit 3 based on the information from an external input/output portion 2. Further, the practical control of the RAM 7 for collation data and the EEPROM 8 for reference data is performed by the controller 4. This controller 4 discharges the duties of a memory controller and a shift register controller.

Besides, a shift clock is applied to the shift register 6 for taking in data from the controller 4.

Next, the positional information group determining means 200 shown in FIG. 3 has such a structure as described hereunder.

The controller 4 is a circuit for controlling transfer of data among a central processing unit (hereinafter referred to as a CPU) 3, a RAM 9 for collation address, a shift register 21 for reference, a RAM 7 for collation data and an EEPROM 8 for reference data. This controller 4 is connected through a data bus DB to above-mentioned RAM 7 for collation address, shift register 21 for reference, RAM 7 for collation data, EEPROM 8 for reference data, and further to a coefficient of collation detecting portion 19 and so on.

The coefficient of collation detecting portion 19 shown in FIG. 3 includes a collation data register 20, a coefficient of collation (also referred to as a coefficient of coincidence) threshold setting register 22, a coefficient of collation detecting logic circuit 23, a magnitude comparator 24 and so on. A shift register 21 for reference is provided between the coefficient of collation detecting logic circuit 23 and the data bus DB. Further, a RAM 9 for collation address is provided between the CPU 3 and the controller 4.

First, the shift register 21 for reference is a shift register for shifting all of the binary coded image data for reference read out of the EEPROM 8 for reference data consecutively for each line. Line control and so on are performed by means of the controller 4.

The collation data register 20 stores one-dimensional information (also referred to as one-dimensional data) extracted from the RAM 7 for collation data.

Figure 4:
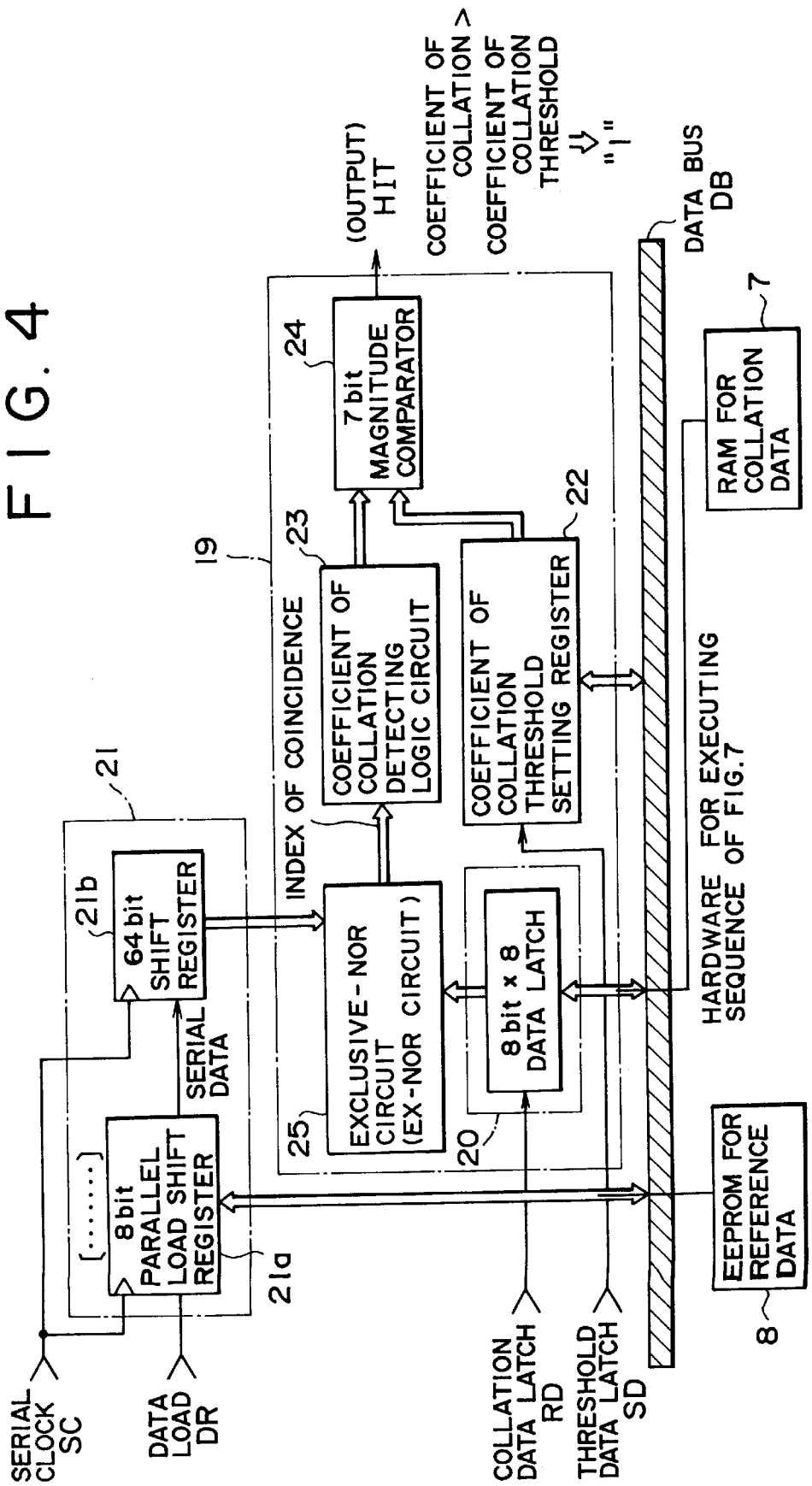
FIG. 4 is a block diagram of a collating portion in the system block diagram shown in FIG. 3.

The coefficient of collation detecting logic circuit 23 is a logic circuit for detecting corresponding respective bits of the shift register 21 for collation and the collation data register 20 to find whether logics are in accord with each other by means of an exclusive nor (ex-nor) circuit 25 shown in FIG. 4 and outputs whether logics are in accord with one another in several bits among the compared bits.

In short, the coefficient of collation detecting logic circuit 23 is a circuit for counting how many of 64 pieces of ex-nor circuits 25 are at "1", and is an encoder for converting 64 bits into 7-bit parallel data.

The coefficient of collation threshold setting register 22 is a register for setting the threshold for the bit number when the logics detected by the coefficient of collation detecting logic circuit 23 are in accord with one another.

The magnitude comparator 24 compares magnitudes of 7-bit data of the coefficient of collation threshold setting register 22 and 7-bit data of the coefficient of collation detecting logic circuit 23 with each other, and outputs an output (HIT) "1" when the coefficient of coincidence (coefficient of collation) exceeds the threshold (coefficient of collation>coefficient of collation threshold). This output logic is referred to as HIT.

The RAM 9 for collation address is a memory for storing the address of a collation image as a positional information group in collation images when the output logic HIT outputs "1", in a word, when the number of coincidence of the data of one-dimensional information exceeds the threshold.

The ex-nor circuit 25 is composed of 64 pieces of ex-nors, and detects coincidence of respective data in 64 bits. In the case of coincidence, logic "1" is shown, and in the case of disagreement, logic "0" is shown.

As described, the positional information group determining means 200 shown in FIG. 3 collates plural pieces of one-dimensional information that are collation images with images for reference, thereby to obtain the positional information groups at locations where the coefficient of coincidence of data with respect to respective one-dimensional information reaches a set value or higher.

The shift register for reference 21 shown in FIG. 3 has an 8-bit parallel load shift register 21a and a 64-bit shift register 21b as shown in FIG. 4. The shift register 21a is a circuit for latching parallel data read out of EEPROM 8 for reference data and converting them into serial data, and the shift register 21b shifts the data of each line of reference data consecutively in the X-direction. This shift register 21b—is connected to the exclusive-nor circuit 25. Further, the collation data register 20 is connected to the exclusive-nor circuit 25. The parallel load shift register 21a takes in binary-coded image data for reference from the EEPROM 8 for reference data through the data bus DB based on a serial clock SC when the data load DR is given. Further, the collation data register 20 performs 8-bits×8 data latch, and stores (latches) one-dimensional information extracted from the RAM 7 for collation data through the data bus DB based on the collation data latch RD. In a word, the collation data register 20 latches 64-bits of one-dimensional information for collation.

Furthermore, the coefficient of collation threshold setting register 22 is capable of setting the threshold of a predetermined coefficient of collation from the CPU 3 through the data bus DB based on the threshold data latch SD.

Besides, the memory controller portion of the controller 4 shown in FIG. 3 controls the shift of the shift register 21 for reference and the shift register 6,—and the memory controller portion of the controller 4—controls transfer of data among shift registers 21a and 21b, memories, various registers and the CPU 3.

The CPU 3 has such functions as follows. That is to say, the CPU 3 extracts one-dimensional information from data for collation that are stored in the RAM 7 for collation data and puts the information in the collation data register 20. Further, when the positional information group determining means 200 collates these one-dimensional information with images for reference of the object, thereby to obtain positional information groups at locations where the coefficient of coincidence of the data reaches a set value or higher with respect to respective one-dimensional information, the CPU 3 decides that the image for collation and the image for reference are identical when a combination of data having a relative positional relationship which coincides with the relative positional relationship of the extracted one-dimensional information or is within prescribed dispersion exists among positional information groups obtained with respect to respective one-dimensional information. Furthermore, the CPU 3 executes various algorithms.

Next, an operation example of the above-mentioned apparatus for collating images will be described.

Figure 6:
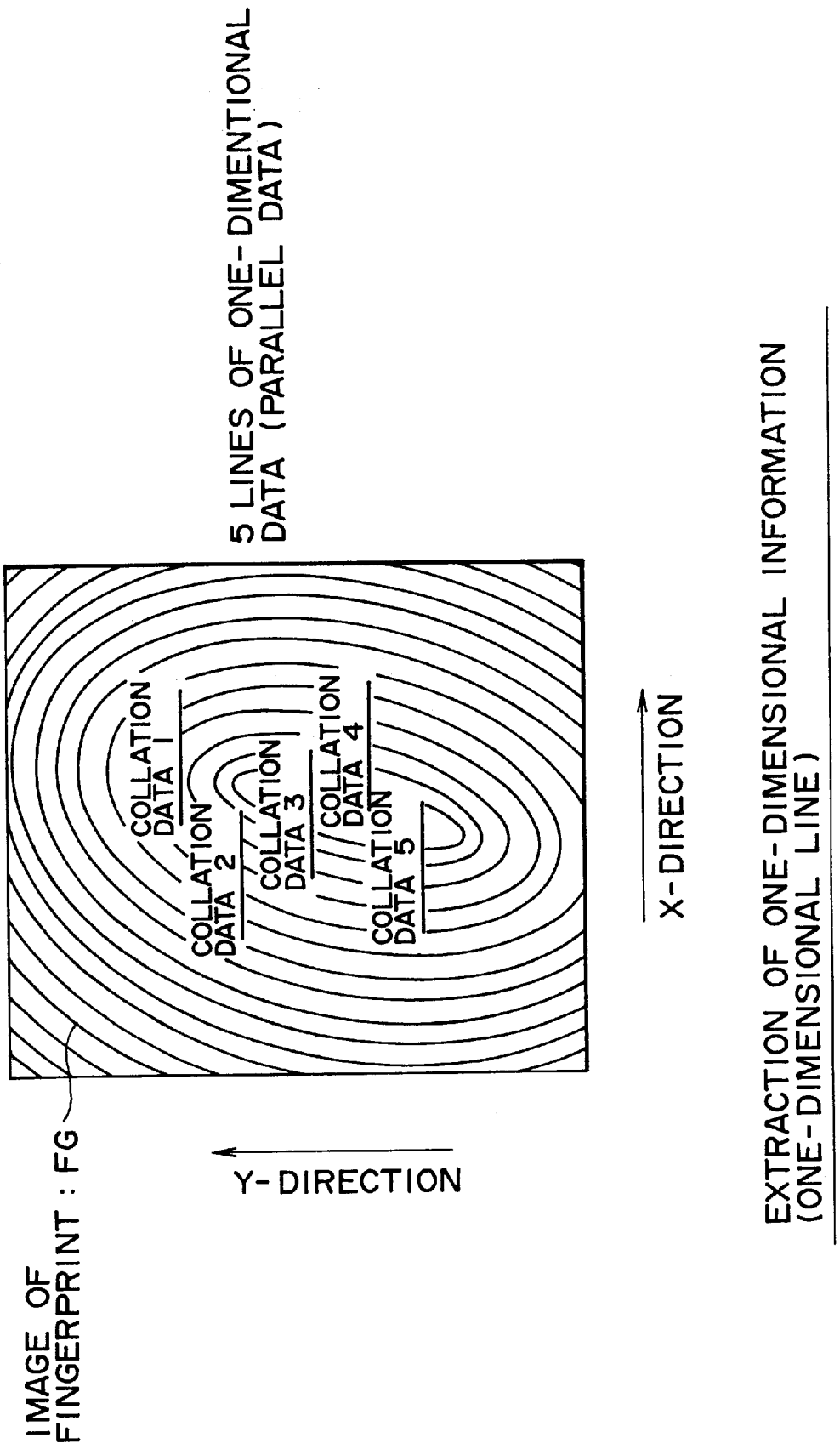
FIG. 6 is a diagram for explaining extraction of one-dimensional information of a taken-in image of a fingerprint.

First, reference is made to FIG. 6. FIG. 6 shows an example of extracting five lines of one-dimensional information (one-dimensional data) 64 bits long from the image FG of one fingerprint shown in FIG. 2. These five lines of one-dimensional information are to be called collation data 1 to 5. Here, it is assumed that the positional relationship among collation data 1 to 5 are parallel (or almost parallel) to one another as shown in FIG. 6.

Figure 8A:
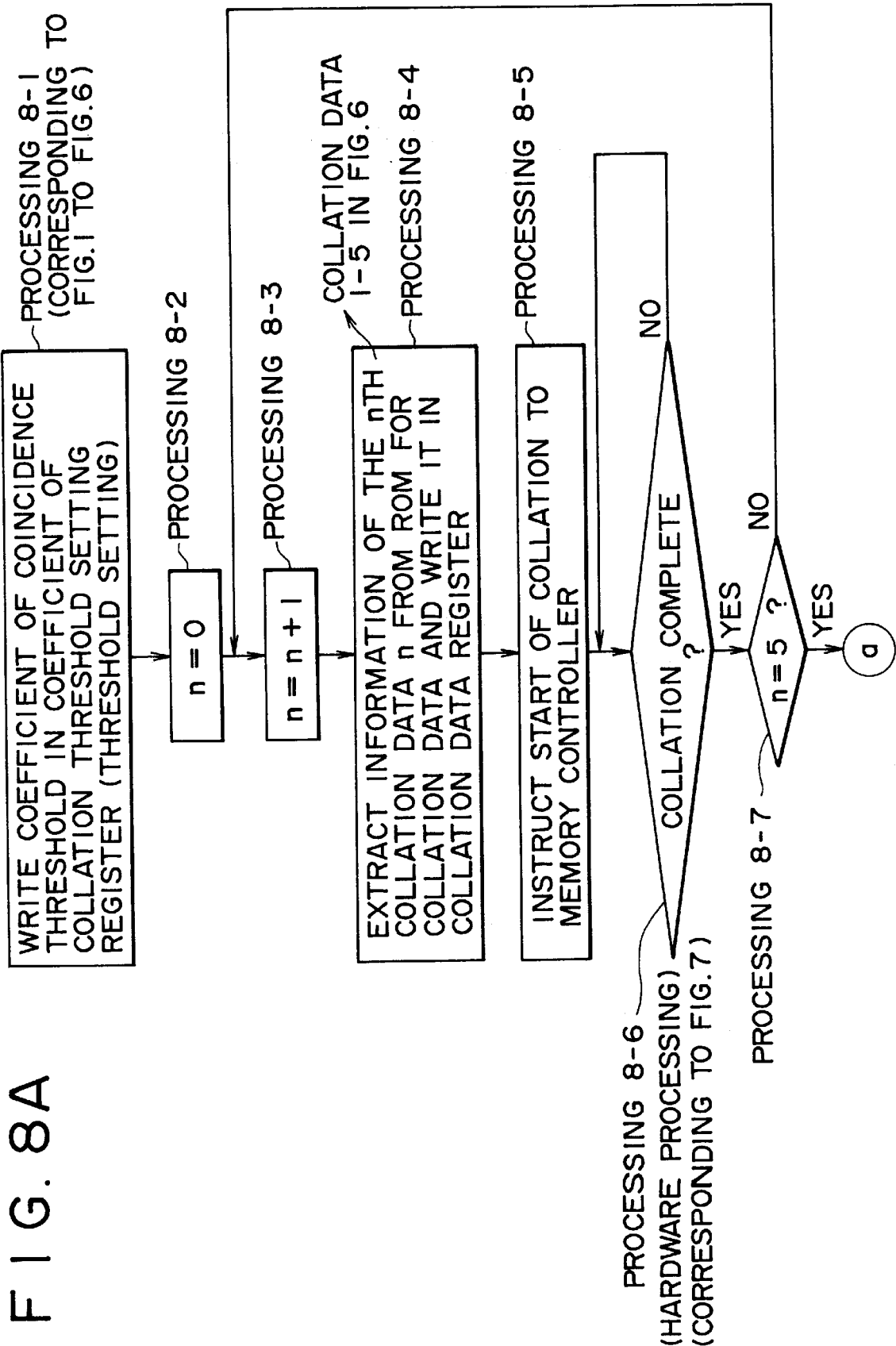

FIG. 8 shows a sequence of collation of an image of a fingerprint when an apparatus for collating images is used.

In the processing 8-1 shown in FIG. 8, a threshold which is a predetermined set value is set in the coefficient of coincidence (coefficient of collation) threshold setting register 22. Since the number of collation bits of respective collation data 1 to 5 in FIG. 6 is 64 bits, the number of bits as the threshold becomes 48 when the threshold is 75%, and the number of bits is set to 58 when the threshold is 90%. The higher this value is, the more strict coincidence is required. Thus, the accuracy of the collation operation is improved. In this case, however, decision is not made as coincidence even for a slight change of an image. When such a fact is taken into consideration, it depends on the quality and the state of an image, but it is suitable that the threshold is 70% to 95% in an image collation operation including dispersion such as detection of a fingerprint. The setting of the threshold is executed by the CPU 3 shown in FIG. 3 writing data in the coefficient of collation threshold setting register 22.

Next, in the processing 8-2 shown in FIG. 8, 0 is substituted for n as an initial value of a collation data number n. Then, in the processing 8-3, n is incremented by 1, and in the processing 8-4, the data having the collation data number n are read out of relevant coordinates of the RAM 7 for collation data (shown in FIG. 3), and these collation data are stored in the collation data register 20 shown in FIG. 3. The collation data 1 to 5 that are one-dimensional information (one-dimensional data) shown in FIG. 6 are read out by the CPU 3 making access to pertinent coordinates of the RAM 7 for collation data through the data bus DB. Namely, this processing is executed by storing data in 64 bits that have been read out to the collation data register 20 as 8-bits×8 data latch in FIG. 4.

When this setting is completed, the CPU 3 shown in FIG. 3 gives instructions to start collation to the controller 4. When this collation start instruction is detected, the controller 4 starts collation of a fingerprint hardware wise (processing 8-5 shown in FIG. 8).

Next, collation of processing by means of hardware in the processing 8-6 shown in FIG. 8 will be described.

Figure 7:
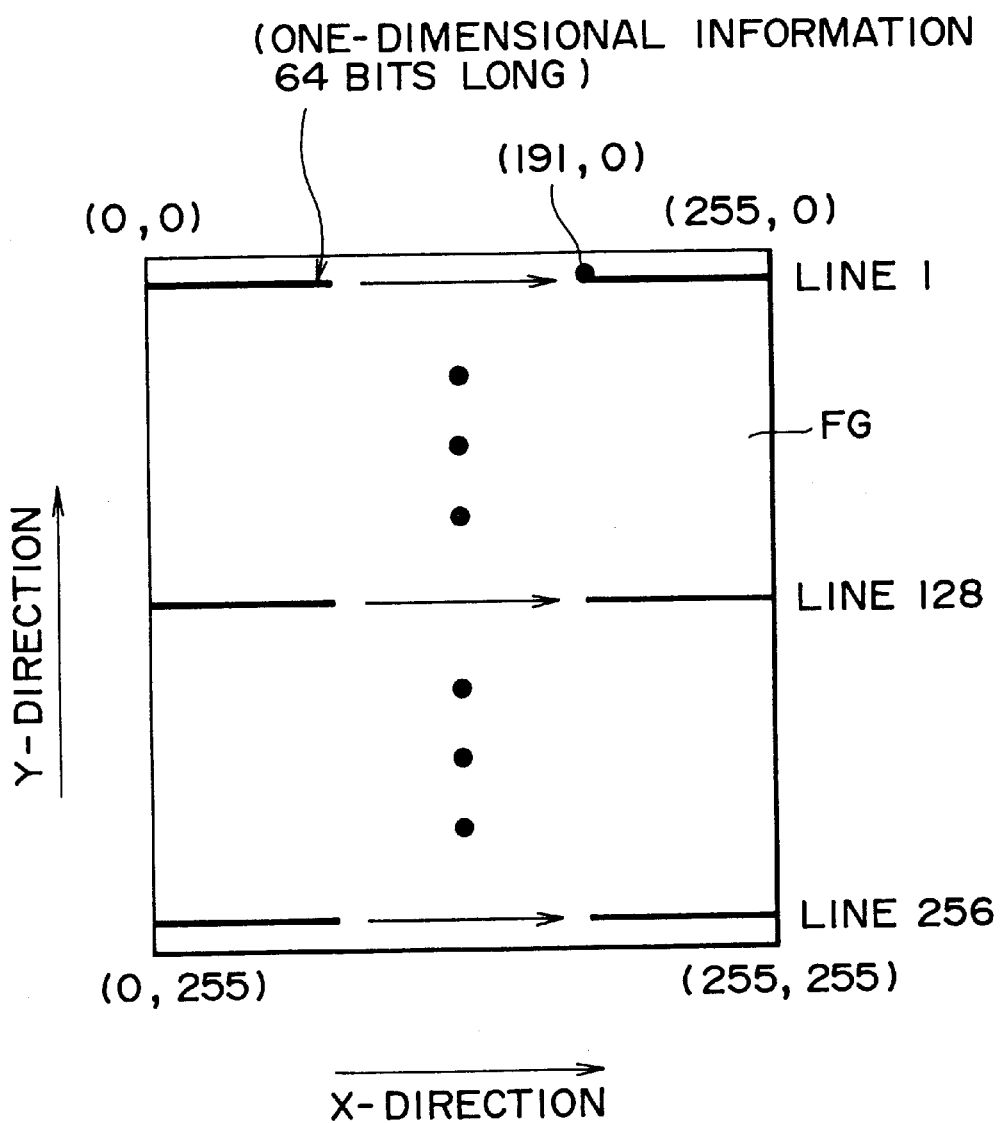
FIG. 7 is a diagram showing the principle of collation of one-dimensional information with an image.

FIG. 7 shows an image for collation by means of hardware. Now, when it is assumed that a data line in the X-direction where Y coordinates are identical is referred to as a line, and a line where Y is 0 is referred to as a line 1 and a line where Y is 1 is referred to as a line 2, 256 lines in total, line 1 to line 256, exist in the image FG of the fingerprint. Black thick lines in FIG. 7 show one-dimensional information 64 bits long.

The collation is started from a location at coordinates (0, 0) of the first line 1. First, the coefficient of coincidence at the coordinates (0, 0) in the first line 1 is detected, and then, the coefficient of coincidence with collation data and reference data in the line 1 is detected while shifting to coordinates (1, 0), then to coordinates (2, 0), . . . , then to coordinates (191, 0) successively.

It is possible to collate one-dimensional information for collation extending over all the images for reference by repeating, when the detection of the coefficient of coincidence in the line 1 is completed, the similar sequence for the line 2, the line 3, the line 256. In this case, the coordinates that the coefficient of coincidence (coefficient of collation) detected during collation is at the coefficient of coincidence (coefficient of collation) threshold or higher are stored hardware wise in the RAM 9 for collation address shown in FIG. 3.

FIG. 4 is a block diagram of the hardware for realizing collation of one-dimensional information shown in FIG. 7. This hardware starts the operation by the instruction to start collation from the CPU 3 shown in FIG. 3 as shown in the processing 8-5 shown in FIG. 8.

First, the controller 4 shown in FIG. 3 has coordinate (0, 0) data outputted from the EEPROM 8 for reference data shown in FIG. 3, and latches data to the 8-bit parallel load shift register 21*a* shown in FIG. 4. These data are shifted successively and coordinate (8, 0) data are outputted when the data are shifted by 8 bits, and these 8-bit data are latched to the parallel load shift register 21*a*. In such a manner, shift and load of data are performed successively, and the first coefficient of coincidence (coefficient of collation) is detected when shifted by 64 bits in a 64-bit shift register 21*b*. The collation at this point (location) is to be referred to as detection of the coefficient of coincidence (coefficient of collation) at the coordinates (0,−0).

This coefficient of coincidence (coefficient of collation) is detected by comparing respective bits of 64 bits of the shift register 21*b* with respective bits of collation data latched by the collation data register 20 by means of the exclusive-nor (ex-nor) circuit 25 and encoding the result thereof by means of the coefficient of collation detecting logic circuit 23. This coefficient of collation detecting logic circuit 23 which is an encoder has a logic of converting the number of logic "1" of the exclusive-nor circuit 25 into data of 7 bits. Accordingly, when the data for collation from the collation data register 20 and the data for reference from the shift register 21*b* of the shift register 21 for reference coincide 100% with each other, 40 hex (corresponding to 40 with a hexadecimal numeral and to 64 with a decimal numeral) is outputted by the coefficient of collation detecting logic circuit 23, and, when those data coincide 50% with each other, 20 hex is outputted to a magnitude comparator 24 by the coefficient of collation detecting logic circuit 23.

It is possible to execute detection of the coefficient of coincidence in the first line 1 shown in FIG. 7 by executing while shifting by one bit at a time in the X-direction. In this case, although the number of bits in the X-direction in the line 1 is 256, detection in 192 times is executed with respect to the line 1 since there is overlapping of 64 bits. This corresponds to detection of the coefficient of coincidence from (0, 0) to (191, 0) in point of coordinates.

The magnitude comparator 24 shown in FIG. 3 and FIG. 4 decides whether the encoded coefficient of coincidence is at a predetermined threshold or higher. Here, the magnitudes of the output of the coefficient of collation detecting logic circuit 23 and the threshold data from the coefficient of collation threshold setting register 22 are compared with each other, the output (HIT) at "1" is outputted. When the output (HIT) reaches "1", the controller 4 shown in FIG. 3 writes the coordinates of the image at that time contained therein in the RAM 9 for collation address.

By means of this sequence, collation with one-dimensional information in the line 1 can be made. It is possible to perform collation of one-dimensional collation data with respect to all of the reference images by repeating, when the collation of the line 1 is completed, the same sequence with respect to lines 2 to 256 successively thereafter. The contents of the RAM 9 for collation address at a point of time when collation of all of the images is completed are such that the coefficient of coincidence in all of the images shows coordinates at the threshold or higher. Namely, the data in reference images having a predetermined coefficient of coincidence with respect to one-dimensional collation data are extracted. The completion of collation by means of hardware can be detected by a flag from the controller 4 to the CPU 3 or interruption to the CPU 3.

Next, when the completion of collation of collation data 1 by means of hardware is detected, it is decided in the processing 8-7 shown in FIG. 8 whether n=5 or not. Since n=1 now, the process is returned to the processing 8-3 again, and similar collation work is executed with respect to collation data 2 this time. By executing such a sequence successively until n=5 is reached, collation with reference images is made with respect to collation data 1 to 5 shown in FIG. 6.

When n=5 is reached and the process is shifted to the processing 8-8, it means that the information of all of the addresses (coordinates) that the coefficient of coincidence has exceeded the threshold during collation of collation data 1 to 5 is stored in the RAM 9 for collation address shown in FIG. 3.

In the processing 8-8, the CPU 3 checks whether a combination of data having a relative positional relationship which is the same as the relative positional relationship of respective one-dimensional information that is extracted collation data or within a fixed extent of dispersion exists or not among address groups (positional information groups) of reference images for respective one-dimensional information stored in the RAM 9 for collation address.

Now, it is assumed that the number of addresses (coordinates) that have exceeded the threshold for the collation data 1 to 5 in the processing 8-8, that is to say, the number of positional information is a1 to a5 pieces, respectively, and respective address data are inscribed as ADRS (c, d). Here, it is assumed that c indicates collation data 1 to 5, and d indicates the number among reference images collated for respective collation data where the threshold is exceeded. Therefore, the extent of data for c is 1 to 5, and the extent of d is i1 (1 to a1), i2 (1 to a2), . . . , i5 (1 to a5) for collation data 1 to 5, respectively.

Figure 9A:
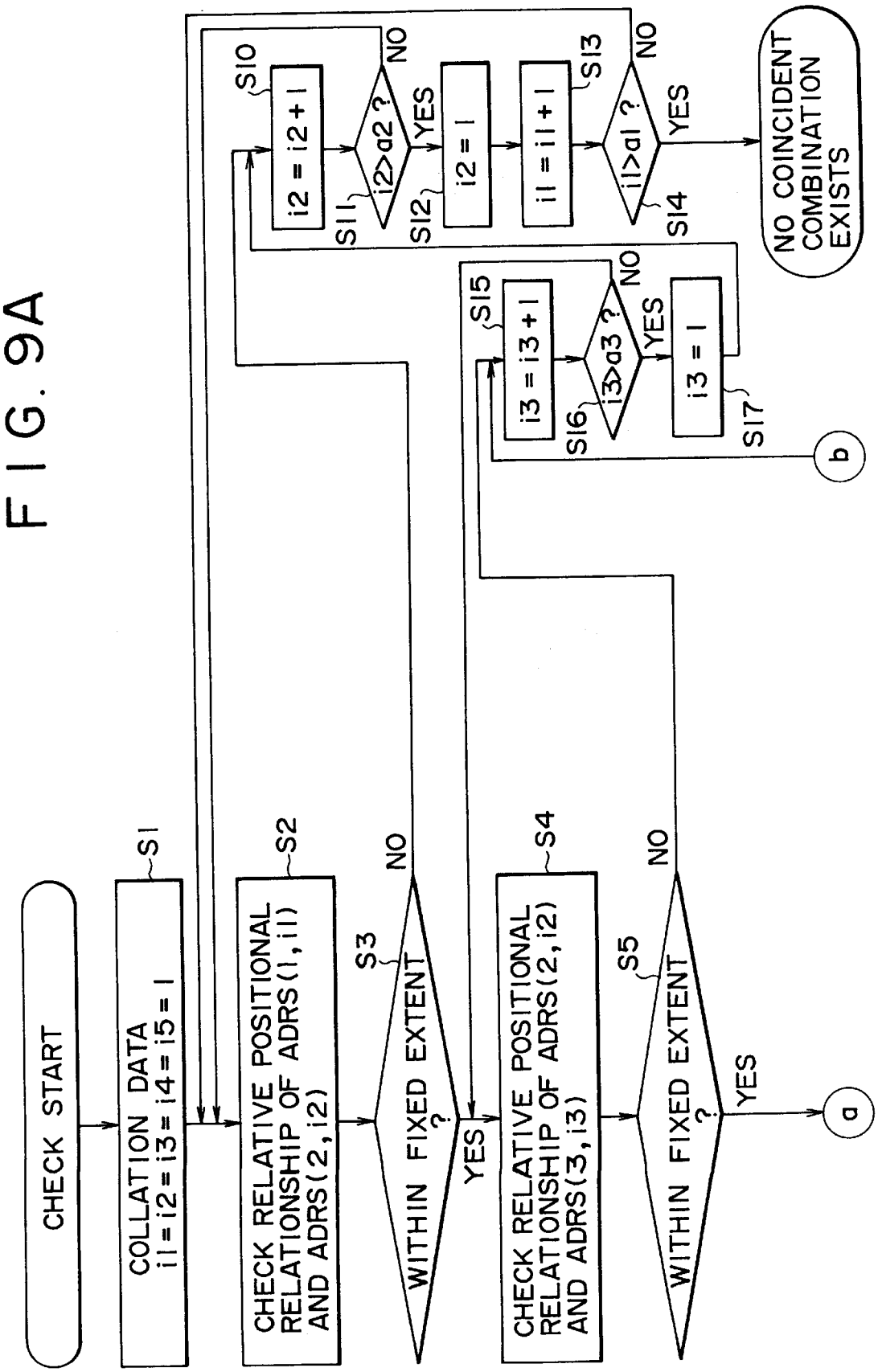
FIGS. 9A and 9B, is a flow chart showing processing 8—8 shown in FIG. 8 in detail.
Figures 9, 9B:
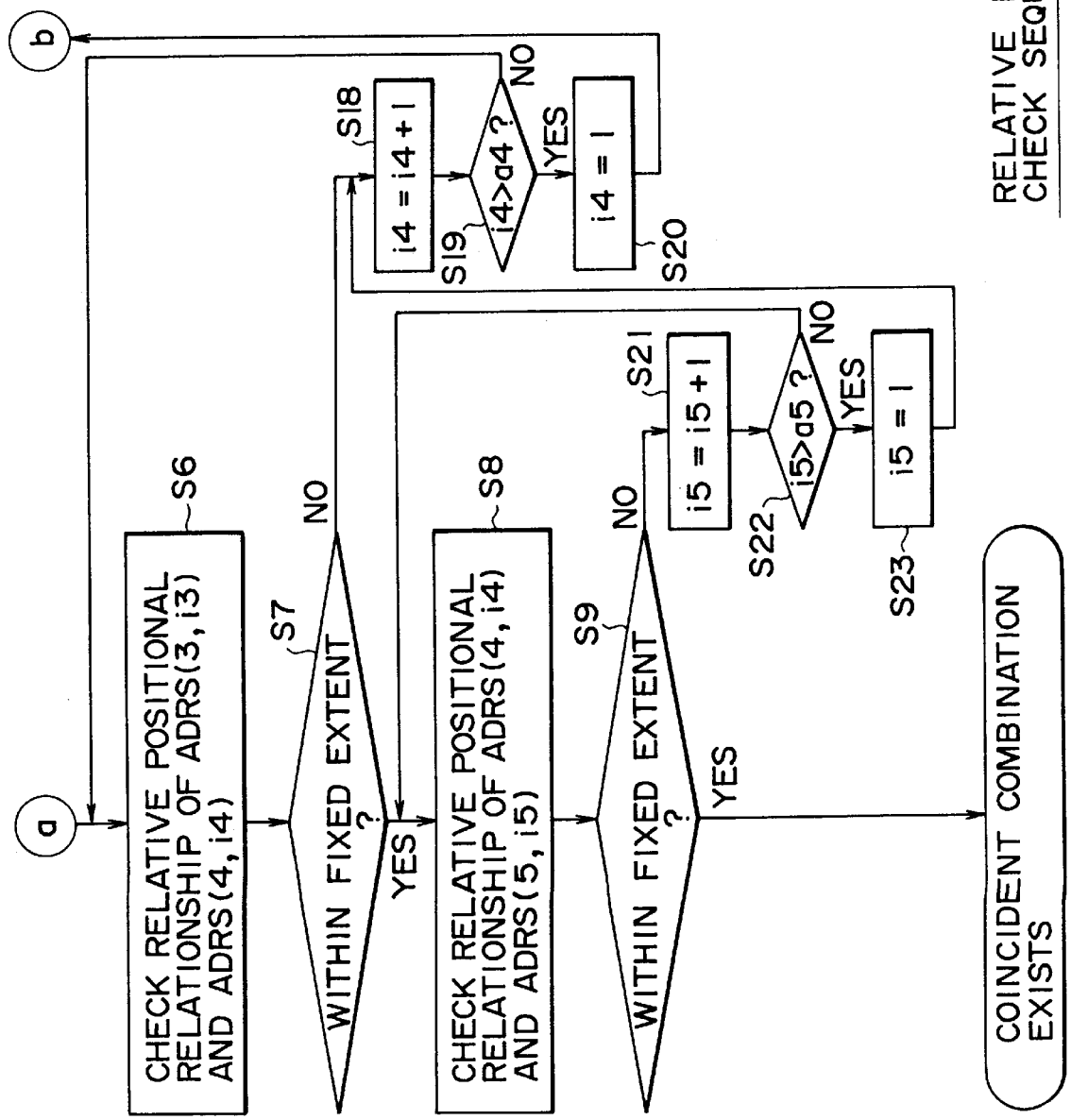
FIG. 9, comprising

FIG. 9 shows a flow chart of this processing. The processing of the flow shown in FIG. 9 is performed by the CPU 3 depending on the contents of the RAM 9 for collation address. That is to say, the CPU 3 decides that the image for collation and the image for reference coincide with each other only when a combination of data having the same relative positional relationship as the relative positional relationship of one-dimensional information exists among all data groups in the sequence shown in FIG. 9.

In the flow shown in FIG. 9, the sequence is brought to an end concluding "a coincident combination exists" when reference image data that have positional relationship coincident to respective relative positional relationships or are within the extent of dispersion exist with respect to respective relative positional relationships of collation data (one-dimensional information) 1 to 5 among respective reference image data obtained as the result of collation, and the sequence is brought to an end concluding "no coincident combination exists" when reference image data within a certain dispersion extent do not exist.

The dispersion quantity in this sequence is set depending on a fixed extent quantity of a decision routine that checks whether the dispersion quantity is within a fixed extent.

FIG. 9, checking to respective relative positional relationships of collation data 1 to 5 is started (step S1), relative positions of ADRS (1, i1) and ADRS (2, i2) are checked (step S2), and the process proceeds to the next when these relative positional relationships are within a fixed extent. Namely, relative positional relationships of ADRS (2, i2) and ADRS (3, i3) are checked (step S4), and the process proceeds to the next when these relative positional relationships are within a fixed extent (step S5). The relative positional relationships of ADRS (3, i3) and ADRS (4, i4) are checked (step S6), and the process proceeds to the next when these relative positional relationships are within a fixed extent (step S7). That is to say, the relative positional relationships of ADRS (4, i4) and ADRS (5, i5) are checked (step S8), and such a conclusion that a coincident combination exists is drawn when these relative positional relationships are within a fixed extent (step S9).

In the step S3, when the relative positional relationship is not within a fixed extent, the process is shifted to a step S10 and i2 of ADRS is incremented by one, and, when i2 is larger than a2, i2 is set to 1 for initializing i2 (step S10 to step S12). Then, when i1 is larger than a1 after i1 is incremented by 1, it is decided that there is no incident combination. Similar processings are also performed (steps S15 to S23) in the step S5, the step S7 and the step S9.

In the step S15, comparison data in the third line are incremented by 1. In the step S16, it is checked whether the incremented value is larger than the data number a3 or not. Since there is none that satisfies the positional relationship in the third line when the incremented value is larger than the data number a3, the process is returned to the check of the second line. At this time, i3=1 is substituted in the step S17 for the purpose of initializing i3.

In the step S16, the process proceeds to the step S4 when i3≦a3 in order to check the positional relationship with respect to the data in the third line.

Steps S18 to S20 and S21 to S23 thereafter show the same sequence with respect to line data in the fourth line and the fifth line. It is the CPU 3 shown in FIG. 1 that decides whether a coincident combination exists or not in such relative positional relationship.

When it is found that "a coincident combination exists" as the result of processing 8-9 shown in FIG. 8, the CPU 3 in FIG. 3 decides that the collation image and the reference image coincide with each other. On the other hand, when "no coincident combination exists", the CPU 3 shown in FIG. 3 decides that the collation image and the reference image are images different from each other. By such a sequence as described above, the CPU makes the decision on image coincidence.

Now, in the sequence shown in FIG. 9, it is decided that images coincide with each other only when a combination of data having the same relative positional relationship as the relative positional relationship of extracted one-dimensional information exists among all of the positional information groups (all data groups). In actual image collation, however, the above-mentioned combination does not exist sometimes among all of the data groups because of various disturbance factors. In such a case, the CPU 3 recognizes the same image as a different image, thus lowering collation performance of an apparatus for collating images.

As a countermeasure against such unconformity, it is possible to adopt a system that the CPU 3 is made to decide to be the same image when a combination having a relative positional relationship which is the same as the relative positional relationship of one-dimensional information of extracted collation data or is within a fixed dispersion extent exists among address groups (positional information groups) of collated reference images for one-dimensional information that is respective collation data stored in the RAM 9 for collation address.

For example, in comparison among five lines of one-dimensional information (one-dimensional data), seven lines of one-dimensional data for instance are extracted as collation data and above-described collation is carried out for image collation work capable of sufficient image collation. When a combination that satisfies the above-mentioned relative positional relationship exists in five or more address groups among seven address groups obtained as the result of the data collation, it is decided that the images coincide with each other. Even when it is decided there is no coincidence due to distortion, defect or the like with respect to two or more data of one-dimensional information among seven one-dimensional information, it is possible to correctly decide coincidence between the image for reference and the image for collation.

As described above, since the CPU 3 decides to be the same image when a combination having a relative positional relationship which is the same as the relative positional relationship of extracted one-dimensional information or with a fixed dispersion extent exists among address groups (positional information groups) in a prescribed number or more, it is possible to eliminate the influence due to defect, distortion or the like of a part of the image and improve performance of image collation.

Figure 10:
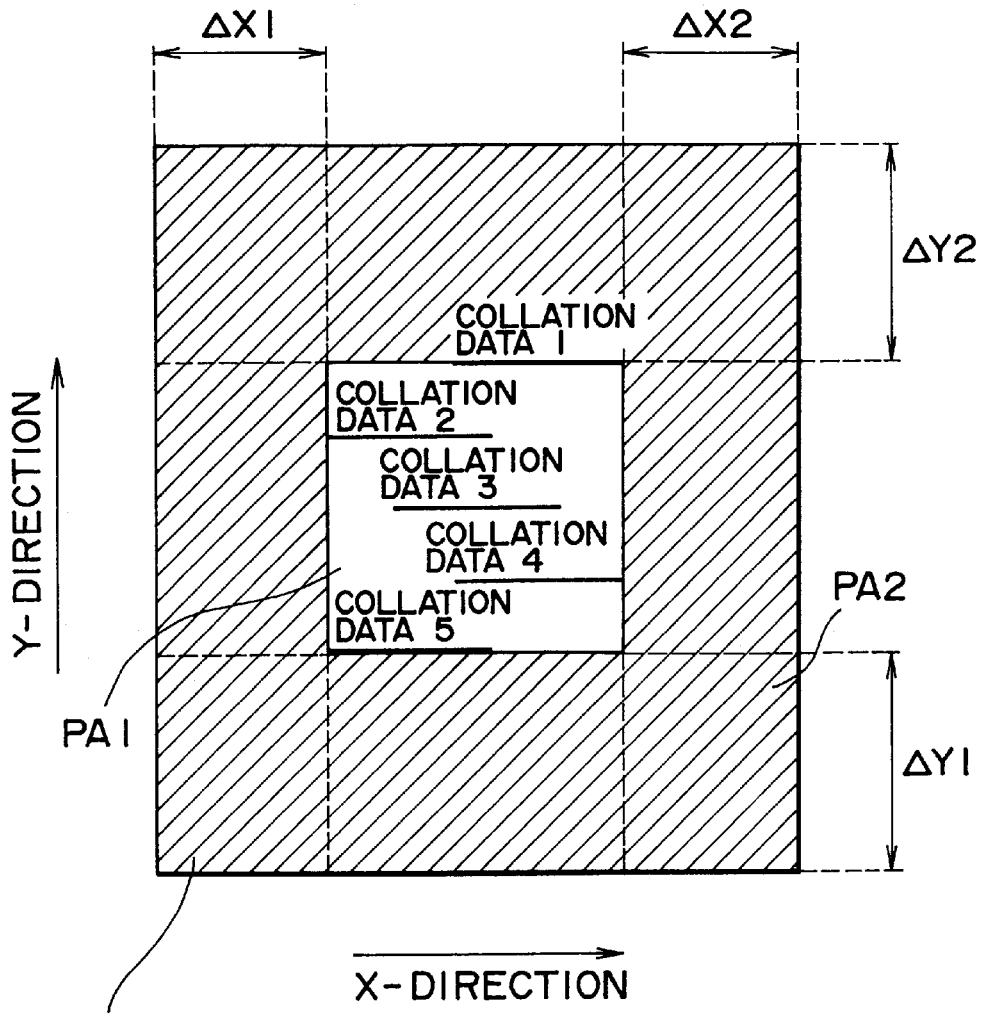
FIG. 10 is a diagram showing an extraction extent of one-dimensional information and an image thereof.

Now, FIG. 10 shows the relationship between an extent PA1 for extracting data for collating one-dimensional information and all image region PA2. As shown in FIG. 10, when the extent of extracting collation data 1 to 5 is set to the extent PA1 for extracting data for collating one-dimensional information which is an extent smaller than the all image region PA2, the outside of the extraction extent of data becomes a permissible extent of a dislocation quantity of the image as shown with oblique lines. The hatched portion in FIG. 10 becomes the permissible extent of dislocation of the collation image and the reference image, and $\Delta X1$ in a minus direction of X, $\Delta X2$ in a plus direction of X, $\Delta Y1$ in a minus direction of Y and $\Delta Y2$ in a plus direction of Y become permissible quantities for dislocation. Since the extraction extent PA1 of one-dimensional information becomes narrower as described above, it is possible to widen the permissible extent of image dislocation. When it is made too narrow, however, the information quantity for collation is reduced and the accuracy of collation is lowered. Thus, it is required to rationalize the extraction extent based on the apparatus for collating images.

Embodiment 2

Next, an embodiment 2 of an apparatus for collating images according to the present invention will be described with reference to FIG. 11. What differs in the embodiment 2 from the embodiment 1 shown in FIG. 3 is the fact that a plurality of coefficient of collation detecting portions 19 are provided. The coefficient of collation detecting portion 19 is also called an collation block, and a plurality of them are provided between a shift register 21 for reference and the data bus DB.

Figure 11:
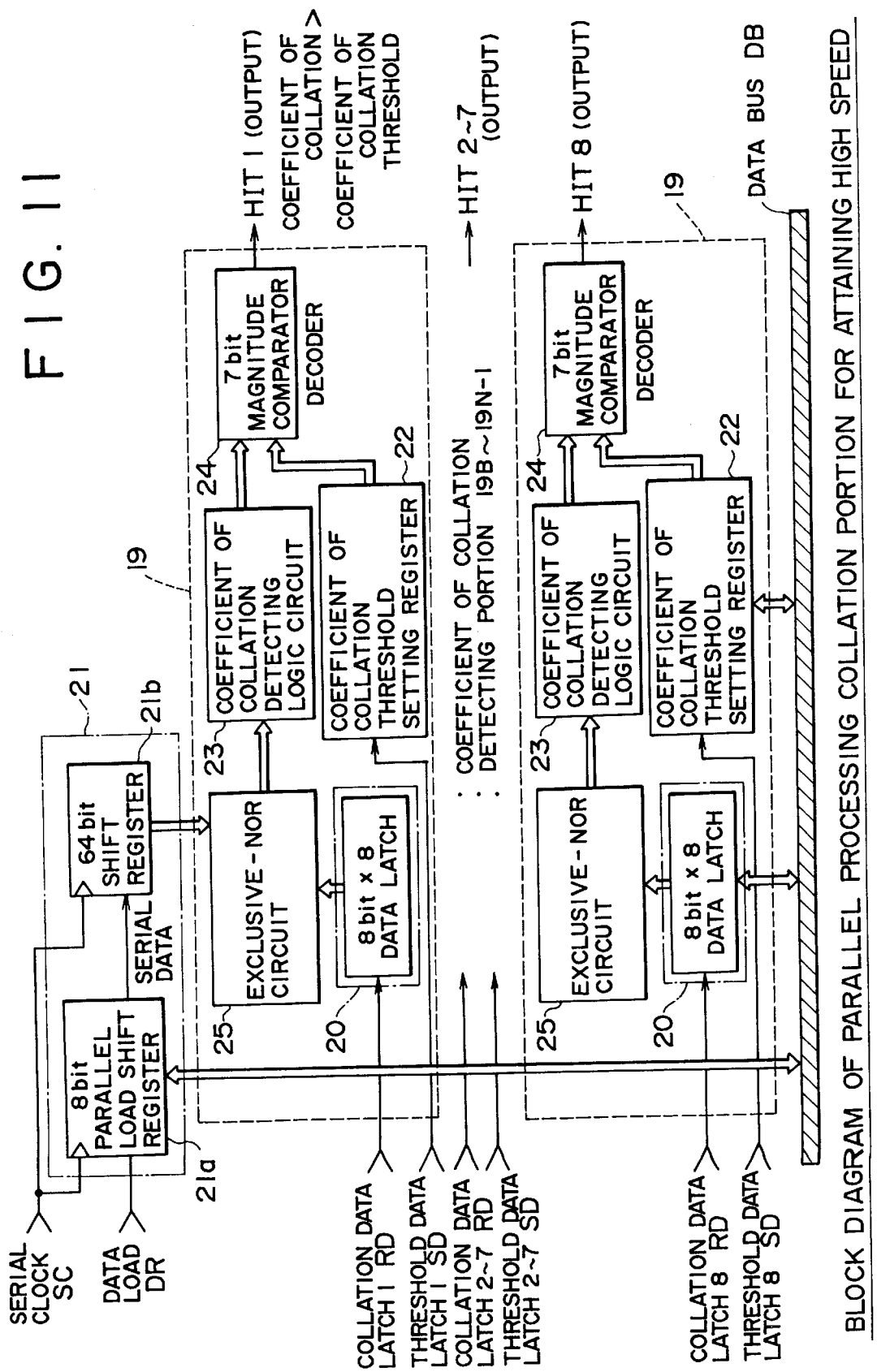
FIG. 11 is a diagram showing an embodiment 2 of the present invention.

As it is apparent from the principle explained in the embodiment 1, a plurality of coefficient of collation detecting portions 19 can execute parallel processing at the same time for data shift of the shift register 21b one time by arranging a plurality of coefficient of collation detecting portions 19 in parallel as shown in FIG. 11. With this, high-speed image collation can be realized. Since eight coefficient of collation detecting portions 19 are provided in the example shown in FIG. 11 for instance, outputs (HIT 1 to 8) can be outputted, thus making it possible to aim at high speed of octuple collation speed. Further, since the coefficient of collation detecting portions 19 are provided in parallel only as a circuit scale required for one parallel processing, there is also such a feature that parallel processing can be realized by slight increase of the circuits.

Since other structure and operation of the embodiment 2 are similar to those in the embodiment 1, description thereof is omitted.

Embodiment 3

Figure 12:
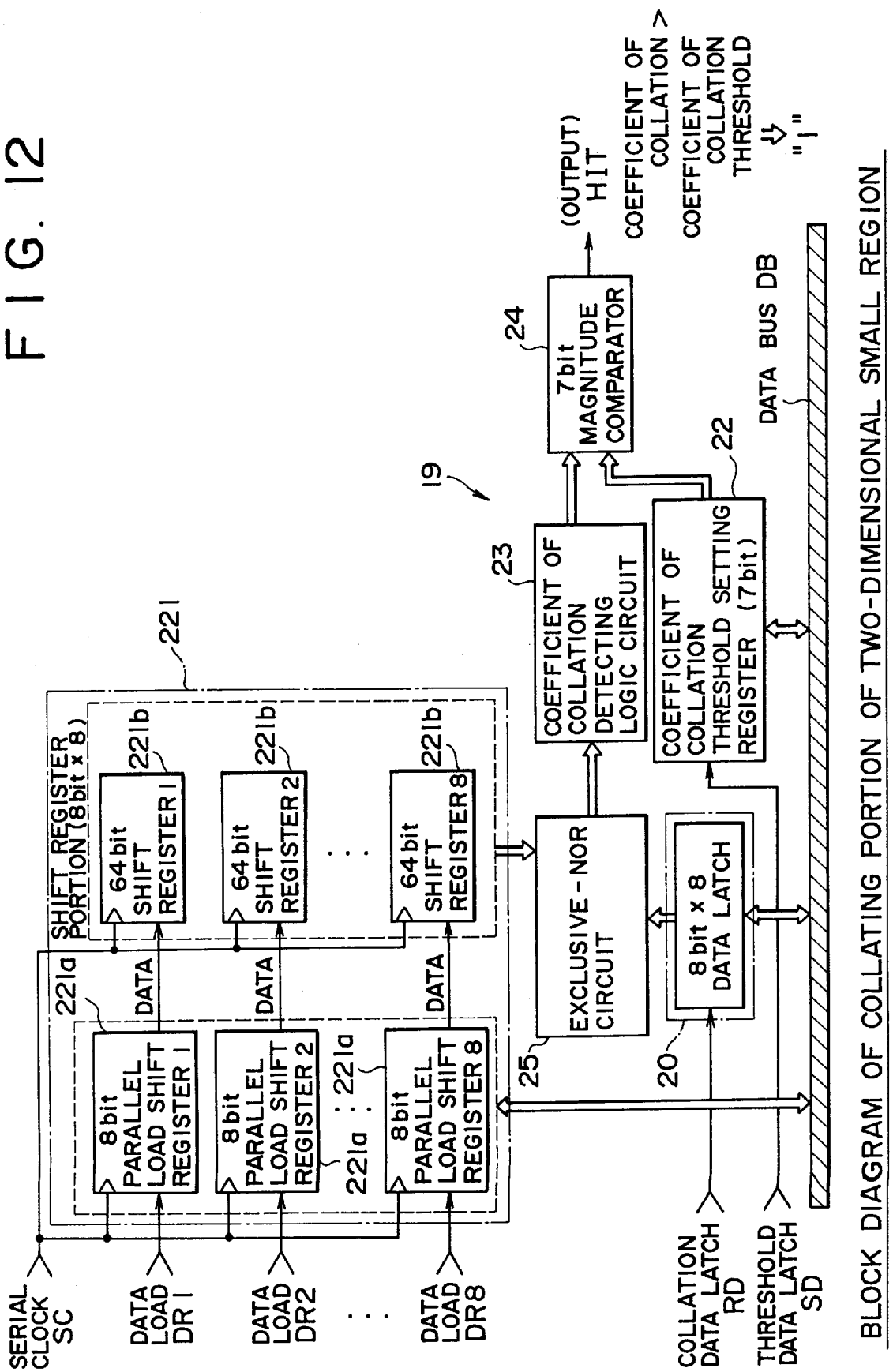
FIG. 12 is a diagram showing an embodiment 3 of the present invention.

FIG. 12 shows an embodiment 3 of an apparatus for collating images. In FIG. 12, similar image collation of a fingerprint is made using a two-dimensional small region extracted from an image for collation. In the embodiment 1 or the embodiment 2, image collation is performed using one-dimensional information of a fingerprint image, but it is possible to execute the same thing using a two-dimensional small region.

In this case, a shift register 221 for reference shown in FIG. 12 is used in place of the 64-bit shift register 21 for reference in FIG. 3. Eight pieces of 8-bit shift registers 221a and 221b are used for this shift register 221 for reference. With this, the two-dimensional small region can be processed in parallel by means of eight pieces of shift registers 221a and eight pieces of shift registers 221b. Further, with respect to the embodiment 3, it is possible to perform parallel processing by providing a plurality of coefficient of collation detecting portions 19 as shown in FIG. 11.

In the embodiments described above, plural pieces of one-dimensional information are extracted from the RAM 7 for collation data, and are collated with the images for reference of the object, thereby to obtain positional information groups at locations (points) where the coefficient of coincidence of data reaches a set value or higher with respect to respective pieces of one-dimensional information. However, it is not limited thereto, but, on the contrary, it may be performed so that plural pieces of one-dimensional information are extracted from the EEPROM 8 for reference data and collated with images for collation of the object, thereby to obtain positional information groups at locations (points) where the coefficient of coincidence of data reaches a set value or higher with respect to respective pieces of one-dimensional information.

In the embodiments of an apparatus for collating images of the present invention, when digital images are collated, plural pieces of one-dimensional information in the image data of the image for collation or the image for reference are collated with another image (image for reference or image for collation), to obtain positional information groups at points where the coefficient of coincidence of the image for collation and the image for reference reaches the threshold or higher. When a combination of data having a positional relationship which coincides with the relative positional relationship of extracted one-dimensional information exists among these respective positional information groups, it is decided that two images have coincided with each other. Besides, according to the present invention, there is such a merit that small amount of storage data quantity is sufficient by storing in a registered image with one-dimensional information (one-dimensional lines). Further, one-dimensional information may be either parallel or almost parallel to each other.

Now, the present invention is not limited to the embodiments described above.

For example, the embodiment of an apparatus for collating images described above is used for collating an image for collation of a fingerprint taken in as digital data with an image for reference of a fingerprint stored as digital data, but this apparatus for collating images can be used as an apparatus for guarding such as for entering into and leaving from (for auto-locking) of aggregate housing. Further, it is applicable to collation of clinical charts and a security system such as prevention of abuse of a credit card or a personal certification system.

What is claimed is:

1. A method of comparing working and reference images stored as digital data comprising:

extracting a plurality of line segment data from the digital data representing the working image, the extracted line segments being noncontiguous and having a relative positional relationship among themselves, wherein said extracted data for each line segment comprises data for each pixel in that line segment of said working image;

comparing each extracted line segment with digital data representing the reference image to identify, by location within said reference image, every line segment from said digital data of said reference image which matches each extracted line segment from said working image to a predetermined degree; and determining that the working and reference images are identical if a match is found for each of said extracted line segments of said working image, wherein the positional relationship among matching line segments from said reference image match said relative positional relationship among said extracted line segments from said working image to a predetermined degree.

2. A method of collating working and reference images stored as digital data according to claim 1, wherein said comparing each extracted line segment from said working image with the digital data representing said reference image is executed in a horizontal direction with overlapping of line segments from said reference image being taken for comparison.

3. A device for comparing collated data from a first image with data from a second image, the device comprising:
   an imaging device for generating digital data representing said first image;
   a processor for extracting a plurality of collated data strings from said digital data representing a plurality of noncontiguous one-dimensional segments of said first image, wherein each of said data strings comprises data for each pixel in a one-dimensional linear segment of said first image; and
   a comparator for comparing each of said plurality of collated data strings with correspondingly sized segments of digital data representing said second image and determining, within a predetermined tolerance, every segment of the second image that matches each collated data string;
   wherein, if a match for each of said plurality of collated data strings is found within said digital data representing said second image in a positional relationship with respect to said second image matching that of said plurality of collated data strings with respect to said first image within a second predetermined tolerance, said first image is determined to match said second image.

4. The device of claim 3, wherein said imaging device comprises:
   a light source;
   a CCD camera; and
   a triangular prism optically coupled between said light source and said camera, said prism presenting a surface from which said first image is taken.

5. The device of claim 3, wherein said first and second images are images of fingerprints.

6. The device of claim 3, further comprising a static memory device for storing said digital data representing said second image, wherein said memory device is connected to said imaging device such that said digital data representing said second image may be generated using said imaging device.

7. The device of claim 3, wherein said comparator comprises:
   a coefficient of collation detecting logic circuit for counting a number of bits which match between one of said collated data strings and a correspondingly sized segment of said digital data representing said second image; and
   a coefficient of collation threshold setting register for setting a minimum count which must be reached by said logic circuit before said collated data string is held to match said segment of said digital data representing said second image.

8. A method of collating working and reference images stored as digital data comprising:
   extracting a plurality of line segment data from the digital data representing noncontiguous one-dimensional portions of the working image, the extracted line segments having a relative positional relationship among themselves;
   comparing each extracted line segment with digital data representing the reference image to identify, by location within said reference image, line segment data from said digital data of said reference image which matches each extracted line segment from said working image to a predetermined degree; and
   determining that the working and reference images are identical if matches are found for each of said extracted line segment of said working image, wherein a positional relationship among matching line segments from said reference image match said relative positional relationship among said extracted line segments from said working image to a predetermined degree;
   wherein said plurality of one-dimensional segments are five data strings of 64 bits each.

9. A method for matching first and second images comprising:
   extracting a plurality of collated data strings from digital data representing said first image, said collated data strings representing a plurality of noncontiguous one-dimensional segments of said first image, wherein each of said collated data strings comprises data for each pixel in a one-dimensional linear segment of said first image; and
   comparing each of said plurality of collated data strings with correspondingly sized segments of digital data representing said second image and determining, within a predetermined tolerance, every segment of the second image that matches each collated data string;
   wherein, if a match for each of said plurality of collated data strings is found within said digital data representing said second image in a positional relationship with respect to said second image matching that of said plurality of collated data strings with respect to said first image within a second predetermined tolerance, said first image is determined to match said second image.

10. The method of claim 9, further comprising generating said digital data of said first image by passing light through a triangular prism to a CCD camera so as to image an object on a surface of said prism.

11. The method of claim 9, wherein said first and second images are images of fingerprints.

12. The method of claim 9, further comprising:
   generating said digital data of said second image; and
   storing said digital data representing said second image in a memory device.

13. The method of claim 9, wherein said comparing comprises:
   counting a number of bits which match between one of said collated data strings and a correspondingly sized segment of said digital data representing said second image; and
   setting a minimum count which must be reached before said collated data string is held to match said segment of said digital data representing said second image.

14. A method for matching first and second images comprising:
   extracting a plurality of collated data strings from digital data representing said first image, said collated data strings representing a plurality of noncontiguous one-dimensional segments of said first image; and comparing each of said plurality of collated data strings with correspondingly sized segments of digital data representing said second image;

wherein, if, within a predetermined tolerance, matches for said plurality of collated data strings are found within said digital data representing said second image in a positional relationship with respect to said second image matching that of said plurality of collated data strings with respect to said first image within a second predetermined tolerance, said first image is determined to match said second image; and wherein said plurality of one-dimensional segments are five data strings of 64 bits each.

15. A device for comparing collated data from a first image with data from a second image, the device comprising:

imaging means for generating digital data representing said first image;

processing means for extracting a plurality of collated data strings from said digital data representing a plurality of noncontiguous one-dimensional segments of said first image, wherein each of said collated data strings comprises data for each pixel in a one-dimensional linear segment of said first image; and comparing means for comparing each of said plurality of collated data strings with correspondingly sized segments of digital data representing said second image and for determining, within a predetermined tolerance, every segment of the second image that matches each collated data string;

wherein, if a match for each of said plurality of collated data strings is found within said digital data representing said second image in a positional relationship with respect to said second image matching that of said plurality of collated data strings with respect to said first image within a second predetermined tolerance, said first image is determined to match said second image.

16. The device of claim 15, wherein said imaging means comprises:

an illumination means;

a camera means; and a surface optically coupled between said illumination means and said camera means from which said first image is taken.

17. The device of claim 15, wherein said first and second images are images of fingerprints.

18. The device of claim 15, further comprising a memory means for storing said digital data representing said second image, wherein said memory means are connected to said imaging means such that said digital data representing said second image may be generated using said imaging means.

19. The device of claim 15, wherein said comparing means comprises:

counting means for counting a number of bits which match between one of said collated data strings and a correspondingly sized segment of said digital data representing said second image; and a coefficient of collation threshold setting means for setting a minimum count which must be reached by said counting means before said collated data string is held to match said segment of said digital data representing said second image.

20. A device for comparing collated data from a first image with data from a second image, the device comprising:

imaging means for generating digital data representing said first image;

processing means for extracting a plurality of collated data strings from said digital data representing a plurality of noncontiguous one-dimensional segments of said first image; and comparing means for comparing each of said plurality of collated data strings with correspondingly sized segments of digital data representing said second image;

wherein, if, within a predetermined tolerance, matches for said plurality of collated data strings are found within said digital data representing said second image in a positional relationship with respect to said second image matching that of said plurality of collated data strings with respect to said first image within a second predetermined tolerance, said first image is determined to match said second image; and wherein said plurality of one-dimensional segments are five data strings of 64 bits each.

* * * * *